United States Patent
Dean et al.

(10) Patent No.: US 8,835,854 B2
(45) Date of Patent: Sep. 16, 2014

(54) METHOD AND DEVICE FOR IR SPECTROSCOPY MEASUREMENTS WITH FIBER OPTIC NEEDLE PROBE

(75) Inventors: Thomas A. Dean, Maple Valley, WA (US); Paul H. Shelley, Lakewood, WA (US)

(73) Assignee: The Boeing Company, Chicago, IL (US)

( * ) Notice: Subject to any disclaimer, the term of this patent is extended or adjusted under 35 U.S.C. 154(b) by 956 days.

(21) Appl. No.: 12/102,256

(22) Filed: Apr. 14, 2008

(65) Prior Publication Data

US 2009/0257046 A1  Oct. 15, 2009

(51) Int. Cl.
| | | |
|---|---|---|
| *G01J 5/02* | (2006.01) | |
| *G01J 3/02* | (2006.01) | |
| *G01J 1/02* | (2006.01) | |
| *G01N 21/35* | (2014.01) | |
| *G01J 3/42* | (2006.01) | |

(52) U.S. Cl.
CPC .............. *G01J 3/42* (2013.01); *G01J 3/0218* (2013.01); *G01N 2201/08* (2013.01); *G01J 1/02* (2013.01); *G01J 2003/425* (2013.01); *G01N 21/3563* (2013.01)
USPC ..................................... 250/341.2; 250/341.8

(58) Field of Classification Search
USPC ....................................................... 250/341.2
See application file for complete search history.

(56) References Cited

U.S. PATENT DOCUMENTS

| | | | | |
|---|---|---|---|---|
| 5,308,983 | A | * | 5/1994 | Milosevic et al. ........ 250/339.07 |
| 5,569,923 | A | * | 10/1996 | Weissman et al. ......... 250/341.2 |
| 5,694,206 | A | * | 12/1997 | Curtiss ............................. 356/72 |
| 6,784,431 | B2 | | 8/2004 | Shelley et al. |
| 6,794,631 | B2 | | 9/2004 | Clark |
| 6,903,339 | B2 | | 6/2005 | Shelley et al. |
| 7,113,869 | B2 | | 9/2006 | Xue |
| 2007/0076212 | A1 | * | 4/2007 | Zuluaga ......................... 356/477 |
| 2009/0011445 | A1 | * | 1/2009 | Hoon et al. ................... 435/7.92 |
| 2009/0310124 | A1 | * | 12/2009 | Thomson ........................ 356/51 |
| 2011/0038580 | A1 | * | 2/2011 | Griffin ............................. 385/33 |

FOREIGN PATENT DOCUMENTS

EP           0358203 A1 *   3/1990  ............... A61B 5/00

* cited by examiner

*Primary Examiner* — David Porta
*Assistant Examiner* — Carolyn Igyarto
(74) *Attorney, Agent, or Firm* — Parsons Behle & Latimer

(57) ABSTRACT

A method of non-destructively determining the condition of a material, said method including providing an elongated probe containing a plurality of optical fibers, said elongated probe coupled to an infrared spectrometer, said tip of said elongated probe positioned near said material, said elongated probe including said tip having a width of less than about 2.0 mm; and, making an infrared spectroscopy measurement of said material by providing infrared light from said infrared spectrometer through at least one of said plurality of optical fibers and collecting at least a portion of said infrared light reflected from a material juxtaposed near said tip through at least another of said plurality of optical fibers to provide said reflected light to said infrared spectrometer.

8 Claims, 3 Drawing Sheets

METHOD AND DEVICE FOR IR SPECTROSCOPY MEASUREMENTS WITH FIBER OPTIC NEEDLE PROBE

FIELD OF THE INVENTION

This invention generally relates to Infrared (IR) spectroscopy measurement methods and apparatus, and more particularly provides a method and device for making Non-Destructive IR spectroscopy measurements with minimal intrusion using a fiber optic needle probe assembly having a measurement end having a width or diameter below a critical size that allows minimal intrusion and the ability to access otherwise hard-to-access or inaccessible samples for IR spectroscopy measurement including evaluation of the condition of aircraft composite materials and/or adhesives used to attach the composite materials together.

BACKGROUND OF THE INVENTION

IR spectroscopy measurements may be useful for a variety of purposes including aerospace, automotive and industrial applications, as well as biological and biomedical applications. For example, infrared (IR) radiation is readily absorbed by organic materials in association with relative motions (vibrations) of atoms such as carbon, hydrogen, oxygen and nitrogen. As such, IR spectroscopy measurements may indicate a condition of a wide variety or organic and inorganic materials.

For example, organic polymer materials such as resin-fiber composites or adhesives may degrade over time due to a variety of reasons including heat exposure. Chemical degradation to a polymer structure may occur, thereby affecting the desired properties of the polymer structure including structural integrity such as strength of a composite or the adhesive properties of an adhesive.

Chemical degradation of a polymer material may be caused by exposure to normal environmental conditions over time, including normal temperature variations and ultra-violet light, as well as exposure to abnormal conditions such as elevated temperatures and stresses, resulting in oxidation and the breaking of existing polymer chemical bonds or forming of new polymer chemical bonds. Maintenance of polymeric materials requires a determination of the degree of degradation of the desirable properties of the polymeric material.

One non-destructive method of ascertaining the condition of polymeric containing material, such as the degree of heat damage to composite materials includes IR spectroscopy of the composite material as outlined in U.S. Pat. No. 7,115,869, which is hereby incorporated by reference in its entirety.

Other non-destructive methods in the prior art include using IR spectroscopy to determine the amount of a chromated conversion coating on a metallic substrate (U.S. Pat. No. 6,794,631), determining the amount of an anodize coating on a metallic substrate, (U.S. Pat. No. 6,784,431), determining and amount of opaque coating on a substrate (U.S. Pat. No. 6,903,339), and determining an amount of heat exposure to a resin-fiber composite substrate (U.S. Pat. No. 7,113,869), all of which are fully incorporated by reference herein.

However, in many cases, organic materials that could benefit from non-destructive IR spectroscopy, cannot be accessed within their normally existing environments by IR spectroscopy measurement methods and devices of the prior art, such as where they must be accessed through a small opening, or where a relatively large sample size must be collected and/or measured ex-situ from a normally existing environment. Thus, many small sampling areas and/or organic materials that are hidden or covered are inaccessible by prior art IR spectroscopy measurement methods and devices making non-destructive evaluation of such materials impractical.

Thus, there is a need for an improved IR non-destructive testing device and method for using the same to non-destructively determine a condition of organic containing materials over small sampling areas and/or in hard-to-access configurations.

Therefore it is an object of the invention to provide an improved IR non-destructive testing device and method for using the same to non-destructively determine a condition of organic containing materials over small sampling areas and/or in hard-to-access configurations.

SUMMARY OF THE INVENTION

In one embodiment a method of non-destructively determining the condition of an organic containing material is provided, said method including providing an elongated probe containing a plurality of optical fibers, said elongated probe coupled to an infrared spectrometer, said tip of said elongated probe positioned near said organic containing material, said elongated probe including said tip having a width of less than about 2.0 mm; and, making an infrared spectroscopy measurement of said organic containing material by providing infrared light from said infrared spectrometer through at least one of said plurality of optical fibers and collecting at least a portion of said infrared light reflected from an organic containing material juxtaposed near said tip through at least another of said plurality of optical fibers to provide said reflected light to said infrared spectrometer.

In another embodiment, a device for making IR spectroscopy measurements in provided, the device including an elongated probe containing a plurality of optical fibers, said elongated probe adapted to be coupled to an infrared spectrometer, said elongated probe including a tip wherein said tip has a width of less than about 2.0 mm; wherein said elongated probe is adapted to perform spectroscopy measurement by providing infrared light from said infrared spectrometer through at least one of said plurality of optical fibers and collecting at least a portion of said infrared light reflected from an organic containing material juxtaposed near said tip through at least another of said plurality of optical fibers to provide said reflected light to said infrared spectrometer.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing an infrared (IR) fiber optic needle probe for accessing small sampling areas and/or hard-to-access or normally inaccessible areas and surfaces for performing non-destructive IR spectroscopy measurements, and a method for performing the non-destructive IR spectroscopy measurements.

It will be appreciated that the IR fiber optic needle probe of the present invention may be suitably used to non-destructively evaluate any organic or polymer containing material as well as inorganic materials, particularly where the sample size desired is on the order of the diameter or width of the IR fiber optic needle probe of the present invention, or where the sample is accessible through a small opening that is larger than the diameter or width of the IR fiber optic needle probe of the present invention.

It will further be appreciated that although the IR fiber optic needle probe of the present invention is explained with exemplary use with respect to a fiber-resin composite material attached to an aircraft surface by an organic adhesive material, such as honeycomb core composite panels, that the IR fiber optic needle probe and method of using the same may be equally applicable to the measurement of any organic or inorganic material having a small sample size and/or accessible through only a small opening, including applications in aerospace, automotive, and industrial fields, as well as biological, medical, and bio-medical fields.

By the terms 'small opening' or 'small sample size', is meant a size on the order of the diameter or width of the measuring end of the IR fiber optic needle probe of the present invention. For example, the IR fiber optic needle probe measuring end preferably has a diameter (or width) less than about 2 mm, more preferably less than about 1.5 mm, and even more preferably less than about 1 mm in diameter. It will be appreciated that the 'small opening' through which the needle is inserted is larger than the measuring end diameter (or width) and that the sampled size is about the same or less than the measuring end diameter (or width).

Figure 1A:
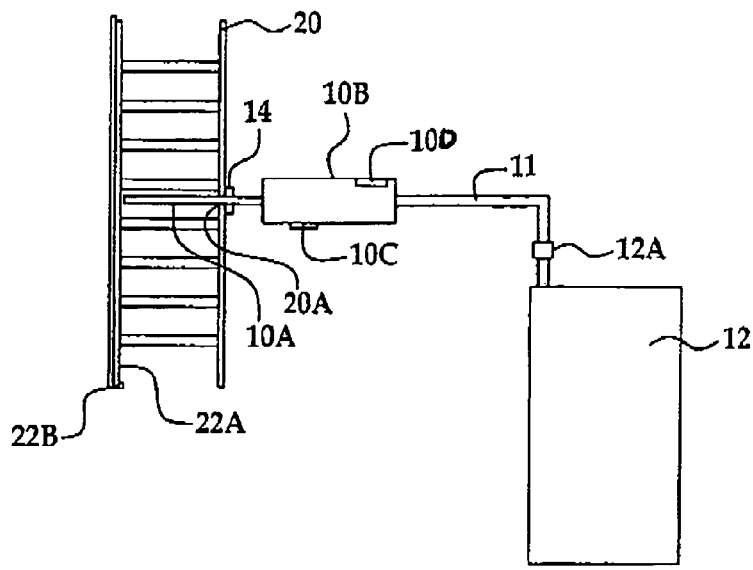
FIG. 1A is a side view of an IR fiber optic needle probe assembly in an IR spectroscopy measurement configuration according to an embodiment of the present invention.

Referring to FIG. 1A is shown a side view of the IR fiber optic needle probe 10 according to an embodiment of the invention. The fiber optic needle probe 10 may be coupled to another fiber optic cable 11, which may in turn may coupled to an IR spectrometer, e.g., 12, through fiber optic coupling connector 12A. The IR spectrometer 12 may be any IR spectrometer that may be interfaced with fiber optics, including a hand-held spectrometer. The IR spectrometer preferably has the capability to perform reflectance measurements, and more preferably, specular reflectance measurements.

It will be appreciated that spectrometer used to make the measurement may use measurement techniques other than specular (i.e., direct reflectance), such as diffuse reflectance. Preferably, the IR Spectrometer includes a multi-frequency infrared source and an infrared detector that includes multi-frequency infrared detection capability. Preferably, the IR spectrometer has the ability to collect measurement spectra over a desired IR frequency range in a short amount of time, for example having a measurement time of less than about 10 seconds, more preferably less than about 5 seconds, even more preferably less than about 1 second.

In an important aspect of the invention, the diameter of the measuring end 11A of the IR fiber optic needle probe 10, preferably having the preferred diameters (or widths) outline above enables the probe to fit through a similarly sized hole (e.g., slightly larger) within an apparatus in order to access a normally inaccessible organic material (e.g. polymer) containing surface.

The IR fiber optic needle probe 10 may include a handle portion 10B, for example having a length and diameter convenient for handling, e.g., form about 3 inches to about 6 inches in length and about, ½ inch to about 2 inches in diameter. The handle portion 10B may include a trigger 10C, such as a depressable switch to trigger an IR spectroscopy measurement and one or more indicator lights e.g., 10D, such as LEDs (light emitting diodes) to indicate the status of a measurement (i.e., one or more of ready for measurement, measuring, and finished with measurement).

In addition, fiber optic needle probe 10 may include a fastener device 14, for example for engaging the outer surface of the measuring end 10A of the fiber optic needle probe 10 and engaging the surface having the opening through which the measuring end of the probe is inserted in order to steady and support the device during measurement if necessary.

The measuring end of the IR fiber optic needle probe 10A may be of different lengths, depending on the application, i.e., the distance required to access a normally inaccessible organic material containing surface. For example, the length of the measuring end of the IR fiber optic needle probe 10A may be from about 1 to about 10 inches in length, more preferably from about 1 to about 5 inches in length, even more preferably about 1 to about 2 inches in length.

The fiber optic needle probe 10 may include one or more optical fibers or bundles of fibers for providing an interrogating IR light source from the tip 10E of the measuring end 10A of the IR fiber optic needle probe 10 and one or more optical fibers or bundles of fibers for collecting IR light reflected off a surface juxtaposed to the tip 10E of the measuring end 10A of the fiber optic needle probe 10.

It will further be appreciated that the fiber optic needle probe 10 as well as the individual optical fibers within the probing portion 10A of the fiber optic needle probe 10 may be tapered along at least a portion of the length of the probing portion 10A, for example tapering from a larger diameter near the handle portion 10B to a smaller final diameter at the tip portion 10E.

Figure 2A:
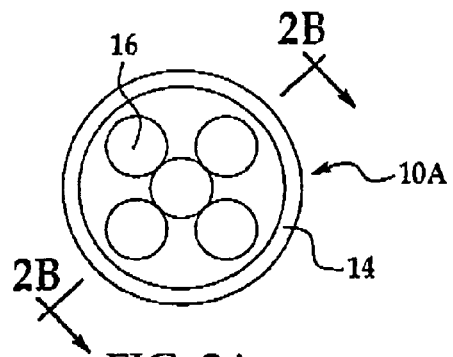
FIG. 2A is a top planar view of a measuring tip end of an IR fiber optic needle probe according to an embodiment of the present invention.

For example, referring to FIG. 2A is shown a planar top view of the front face of the tip 10E of the IR fiber optic needle probe 10. The probe portion 10A of the fiber optic needle probe may include an outer jacket 14 of a resilient material, preferably a metal, for example stainless steel surrounding and containing a plurality of the interrogating optical fibers, e.g., 16. In one embodiment, the outer metal jacket 14 may be stainless steel and have a thickness of about 0.025 to about 0.1 mm. The optical fibers e.g., 16, may provide one or more separate optical fibers for supplying an interrogating IR light source (e.g., outer fibers) and one or more separate optical fibers for collecting the IR light following reflection from an interrogated surface (e.g., central fiber).

It will be appreciated that the optical fibers may be arranged in alternative ways, e.g., such as one or more collecting optical fibers surrounding one or more source optical fibers or where the source and collecting optical fibers are inter-dispersed with one another. The collecting and the source optical fibers may be arranged as individual fibers or bundles of fibers. The individual optical fibers used for collecting and source optical fibers may have the same or different diameters and are preferably in the range of about 10 microns to about 500 microns. The IR optical fibers are formed of an IR transparent material such as silicon, preferably low-OH silicon (dehyroxylated silicon).

Figure 2B:
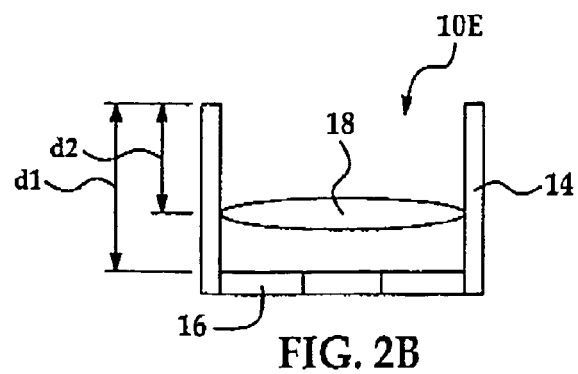
FIG. 2B is a cross sectional view of the measuring tip end of an IR fiber optic needle probe shown in FIG. 2A according to an embodiment of the present invention.

Referring to FIG. 2B, is shown the interrogating tip portion 10E of the probing end 10A of the fiber optic needle probe taken along a cross-section B-B in FIG. 2A. The tip portion 10E may optionally include a window 18 formed of IR transparent material, such as silicon low-OH silicon and may be flat or in the shape of a convex lens set a predetermined distance from both the ends of the optical fibers 16 and the tip 10E (e.g., d2) in order to focus transmitted IR light onto a defined sampling area and/or to focus collected IR light onto one or more collecting optical fibers. Alternatively or in addition, the individual optical fibers e.g., 16, may have ends that are set back a predetermined distance e.g., d1 from the tip 10E of the IR fiber optic needle probe, e.g., a sufficient distance to provide protection if the interrogating end is provided without a window and/or to provide a optimal focus distance if a focusing lens 18 is provided. It will be appreciated that the tip 10E of the IR probe including the jacket 14 may be placed in contact with a surface to be measured (or measurement of a backside of the surface) which may provide further stability for making an IR spectroscopy measurement with the IR probe, particularly when held by hand.

Still referring to FIG. 1A, in exemplary operation, the probe end 10A of the IR fiber optic needle probe 10 is inserted into a small opening (e.g., 1 mm) 20A in an external surface, e.g., backside of honeycomb core composite panel 20 (an aircraft outer portion known in the art), where the hole 20A which may be larger than the probe end 10A. The tip end 10E of the IR fiber optic needle probe 10 is shown arranged to be proximate a surface to be measured, such as a polymer containing surface (e.g., backside surface of composite panel 22), for example, including an adhesive 22A (e.g., adhesive for holding composite panel 20 to composite face sheet 22B.

Figure 1B:
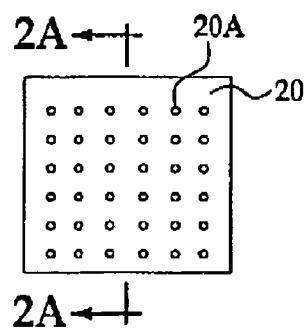
FIG. 1B shows a backside surface of organic containing material e.g., a portion of a honeycomb core composite panel included in the measurement configuration of FIG. 1A according to an embodiment: of the present invention.

For example, FIG. 1B show a portion of the backside of a honeycomb core composite panel 20 (e.g., used in an aircraft structure) including a plurality of perforated openings (holes) having a diameter of about 1 mm. A cross section of the honeycomb core composite panel taken in cross section along A-A in FIG. 1B is shown in FIG. 1A where the honeycomb core composite panel 20 is shown having a honeycomb structure adhesively attached by adhesive 22A to composite face sheet 22B. By inserting the probe end 10A of the fiber optic probe 10 through the opening 20A, the tip end 10E may contact the adhesive layer 22A in order to make an IR spectroscopy measurement determining the condition of the adhesive layer 22A holding honeycomb core composite panel 20 to composite face sheet 22B.

It will be appreciated that the tip end 10E of the IR probe may be placed in contact with a first surface (e.g., 22A or that the tip end 10E of the IR probe may be placed near the measured surface without contacting a surface including the measured surface, however, supporting the tip end 10E by contacting a measurement surface is preferred since this will ensure a consistent distance of IR probe parts from the measured surface and result in more consistent and reliable IR spectroscopy measurements. For example, the optimal distance of the optical fibers within the IR probe tip from the surface to be measured will depend in part on the intensity of the light provided by optical fibers, and the light collecting capability of optical fibers within the fiber optic needle probe.

Figure 3:
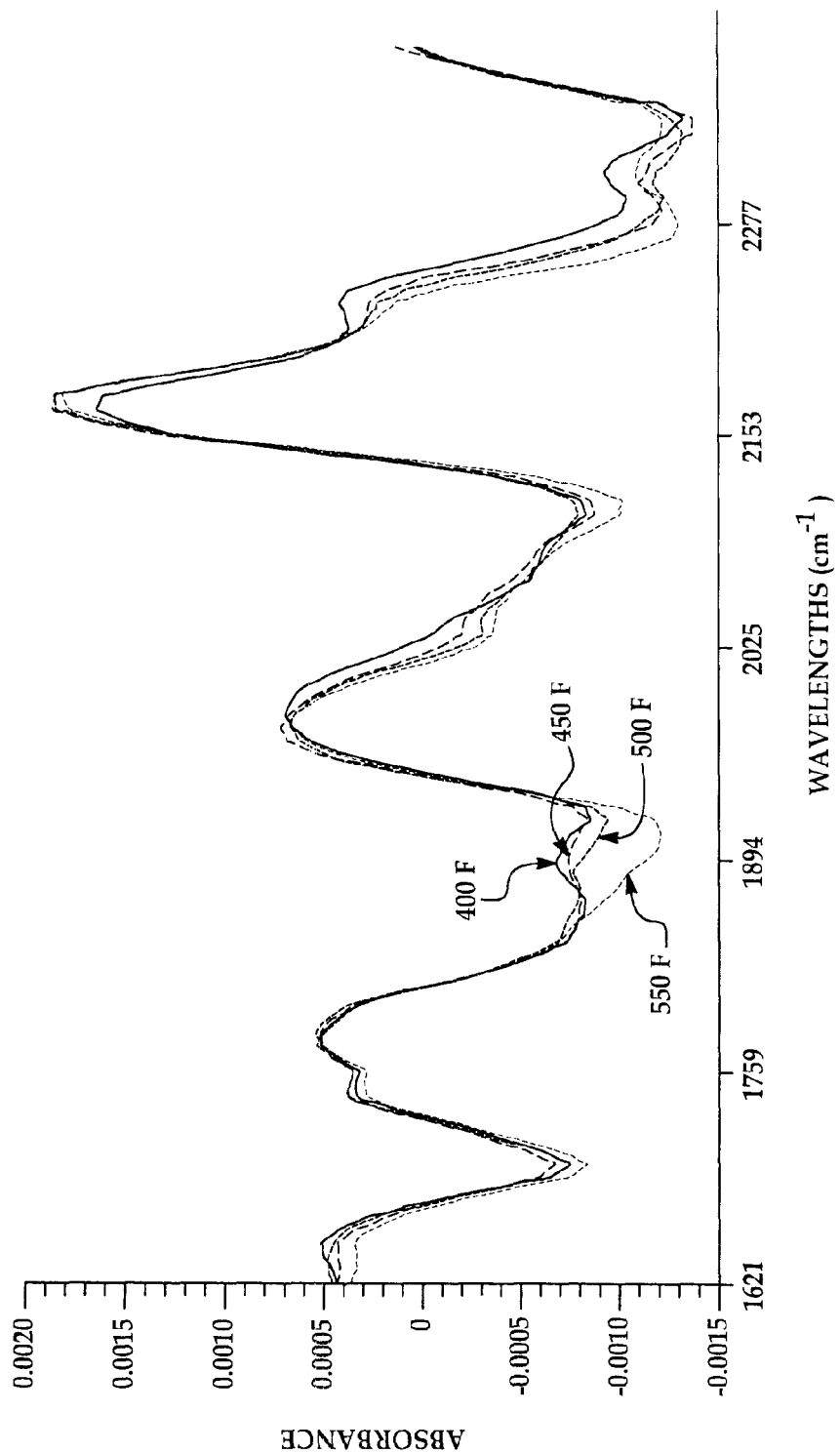
FIG. 3 are exemplary IR Spectra showing exemplary progressive changes an organic containing material over a range of wavelengths according to an embodiment of the present invention.

Referring to FIG. 3 is shown an exemplary calculated Absorbance versus wavenumber (cm-1) spectra e.g., A, B, and C over the range of 4000 to about 500 wavenumbers (cm-1) collected at different time periods showing a progressive relative degradation in a polymer containing material. Although the IR light provided through the IR fiber optic needle probe 10 by spectrometer 12 may include variety of IR wavelength ranges, depending on the spectrometer, the IR wavelength range of the measuring spectrometer preferably includes at least a portion of, and preferably the entire range of, the near infrared wavelength region of about 700 to about 2400 nanometers in wavelength (0.7 to 0.24 microns).

It will be appreciated that the Absorbance is calculated according to well known equations based on the intensity of reflected IR light measured, e.g., a specular reflectance measurement. It will also be appreciated that depending on the wavelength of the region interrogated, that the absorbance peaks represent complex motions of organic materials including the relative motions (vibrations) of atoms such as carbon, hydrogen, oxygen and nitrogen. Thus, depending on the chemical changes associated with degradation of an organic containing material surface, the relative degradation of the organic material may be determined by associating an absorbance (or reflectance) of the surface at a particular wavelength for example above or below a particular acceptable threshold.

For example, evaluation of the IR spectroscopy measurement may be made automatically by a controller included in or connected to the IR spectrometer according to a preprogrammed series of steps including providing an indication (e.g., alarm or signal) indicating unacceptable IR spectroscopy measurement values above or below a predetermined threshold. Alternatively, or in addition, the IR spectroscopy measurement results may be stored in memory included in or connected to the IR spectrometer for later analysis.

In exemplary operation, an organic material containing sample is non-destructively tested by a spectrometer using the IR fiber optic probe to provide IR light and collect the reflected IR light from the tested sample to determine a condition of the organic material containing sample. In one embodiment, a currently collected spectra may be compared with a previously determined threshold spectrum at one or more wavelengths to determine whether the organic material, e.g., adhesive, has acceptable properties or must be replaced or otherwise serviced. For example, spectral information may be included within the spectrometer based on previously determined model spectra for the organic material containing sample, for example an adhesive, where acceptable/unacceptable material properties of the material, for example adhesive properties of the adhesive, have been correlated with threshold absorbance: (or reflectance) values at one or more IR spectroscopy measurement wavelengths.

Figure 4:
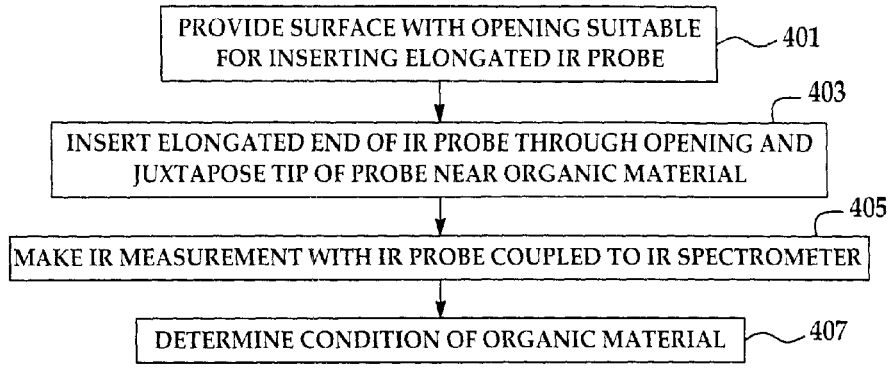
FIG. 4 is a process flow diagram including several embodiments of the invention including using the IR fiber optic needle probe.

Referring to FIG. 4 is shown a process flow diagram including several embodiments of the present invention. In process 401, an opening suitable for inserting the IR fiber optic probe is provided in a surface in order to access a normally inaccessible organic material containing surface. In process 403, a probe tip of the IR fiber optic probe is inserted through the opening and positioned adjacent the organic material containing surface. In process 405, the IR fiber optic probe is coupled to an IR spectrometer and an IR spectroscopy measurement is made by providing one or more wavelengths of IR light through the fiber optic probe to the organic material containing surface and collecting reflected IR light with the fiber optic probe from the organic material containing surface and providing it to the IR spectrometer. In process 407, a condition of the organic material containing surface is determined based on the IR spectroscopy measurement.

Figure 5:
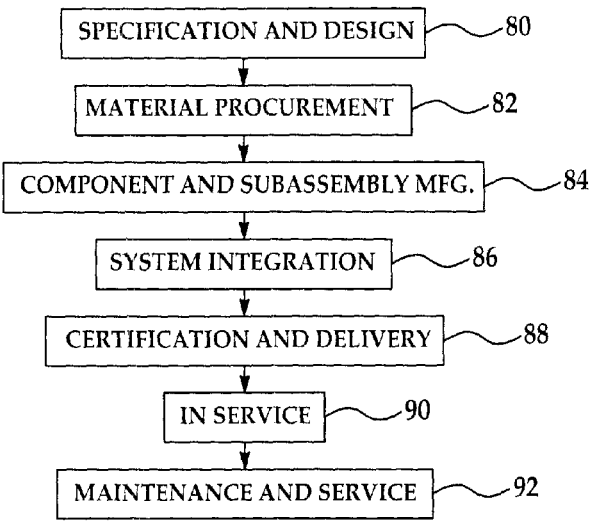
FIG. 5 is a flow diagram of an aircraft and service methodology.
Figure 6:
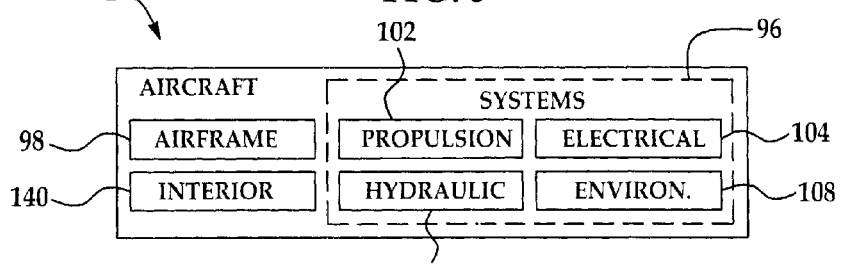
FIG. 6 is a block diagram of an aircraft.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft: manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

It will be appreciated that although the invention is particularly explained with reference to using IR fiber optic probe to perform IR spectroscopy to determine a degree of damage to an organic containing material, the invention may additionally be advantageously used to determine surface conditions of a wide variety of substrates, for example, including determining the thickness of an inorganic opaque material on a substrate, and relative changes in metal substrates such as anodization of a metal or amount of a metal oxide, such as of chromated conversion coating (chromium oxide layer ($Cr_2O_3$)) on a metal substrate.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method for non-destructively determining the condition of a solid polymer-containing material comprising:
providing an elongated needle probe, comprising an outer metal jacket, having a distal tip having an outer diameter of less than 2.0 mm, and containing a plurality of optical fibers having light supplying and light collecting ends positioned a predetermined distance from a distal end of said distal tip, said elongated needle probe coupled to an infrared spectrometer;
inserting said tip of said elongated needle probe through an opening provided in a solid surface to position said tip of said elongated needle probe perpendicularly in contact with a surface of said material; and,
making a near-infrared reflectance spectroscopy measurement of said material by providing infrared light distal from the tip of said infrared spectrometer through at least one of said plurality of optical fibers and collecting at least a portion of said infrared light reflected from said material through at least another of said plurality of optical fibers to provide said reflected light to said infrared spectrometer.

2. The method of claim 1, further comprising a step of determining whether the material is in an acceptable condition based on said infrared spectroscopy measurement.

3. The method of claim 2, wherein the step of determining comprises comparing one or more wavelengths of the infrared spectroscopy measurement to a model infrared spectroscopy measurement.

4. The method of claim 1, wherein said distal tip outer diameter is less than 1.0 mm.

5. The method of claim 1, wherein said infrared light comprises a spectrum of wavelengths of from 700 to 2400 nanometers.

6. The method of claim 1, wherein said outer metal jacket comprises stainless steel.

7. The method of claim 1, wherein said elongated needle probe comprises an IR transparent window positioned a predetermined distance from the distal end of said distal tip.

8. The method of claim 1, wherein said plurality of optical fibers comprises low-OH silicon material.

* * * * *

UNITED STATES PATENT AND TRADEMARK OFFICE
CERTIFICATE OF CORRECTION

PATENT NO. : 8,835,854 B2  
APPLICATION NO. : 12/102256  
DATED : September 16, 2014  
INVENTOR(S) : Thomas A Dean et al.

Page 1 of 1

It is certified that error appears in the above-identified patent and that said Letters Patent is hereby corrected as shown below:

In the Claims

Column 8, Lines 25-27, Claim 1 should read making a near infrared reflectance spectroscopy measurement of said material by providing infrared light from the distal tip of said infrared spectrometer through at Signed and Sealed this  
Twentieth Day of January, 2015

Michelle K. Lee  
*Deputy Director of the United States Patent and Trademark Office*